US009782742B2

United States Patent
Xu et al.

(10) Patent No.: US 9,782,742 B2
(45) Date of Patent: Oct. 10, 2017

(54) INDUCTIVE MAGNETOELECTRIC BIOCHEMICAL REACTION SYSTEM AND APPLICATION THEREOF

(71) Applicant: Jiangnan University, Wuxi (CN)

(72) Inventors: Xueming Xu, Wuxi (CN); Na Yang, Wuxi (CN); Yamei Jin, Wuxi (CN); Nannan Zhang, Wuxi (CN); Dandan Li, Wuxi (CN); Fengfeng Wu, Wuxi (CN); Zhengyu Jin, Wuxi (CN); Yisheng Chen, Wuxi (CN); Xing Zhou, Wuxi (CN); Aiquan Jiao, Wuxi (CN); Jie Ren, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 15/107,064

(22) PCT Filed: Mar. 26, 2015

(86) PCT No.: PCT/CN2015/075098
§ 371 (c)(1),
(2) Date: Jun. 21, 2016

(87) PCT Pub. No.: WO2016/145669
PCT Pub. Date: Sep. 22, 2016

(65) Prior Publication Data
US 2017/0136437 A1 May 18, 2017

(30) Foreign Application Priority Data

Mar. 18, 2015 (CN) .......................... 2015 1 0120034

(51) Int. Cl.
*C12M 1/42* (2006.01)
*B01J 19/08* (2006.01)
(Continued)

(52) U.S. Cl.
CPC ......... *B01J 19/087* (2013.01); *B01D 11/0419* (2013.01); *C12N 13/00* (2013.01);
(Continued)

(58) Field of Classification Search
CPC .... B01J 19/087; B01D 11/0419; C12N 13/00; C12M 23/06; C12M 27/10; C12M 29/18; C12M 35/02; C12M 35/06
See application file for complete search history.

(56) References Cited

FOREIGN PATENT DOCUMENTS

| CN | 202400902 U | 8/2012 |
|---|---|---|
| CN | 103203214 A | 7/2013 |
| JP | 9-236461 | 9/1997 |

OTHER PUBLICATIONS

English translation of CN Office Action published on Jan. 7, 2016.
(Continued)

*Primary Examiner* — William H Beisner
(74) *Attorney, Agent, or Firm* — Wang Law Firm, Inc.

(57) ABSTRACT

An inductive magnetoelectric biochemical reaction system includes a reaction unit which includes a reaction chamber, which includes a reactant container and is disposed in a rotatable perpendicular magnetic field; a primary coil, which is wound around one side of a closed-loop iron core and is connected to a control unit; a secondary coil, which is wound around the other side of the closed-loop iron core and includes an insulating tube which allows a reaction solution acting as a conductor, two ends of the insulating tube being communicated with the reactant container; a rotating magnetic field unit, which is configured to generate the rotatable perpendicular magnetic field; and a control unit, which is at least configured to adjust an excitation voltage and a signal type applied on the primary coil.

13 Claims, 5 Drawing Sheets

(51) Int. Cl.
  *C12N 13/00*  (2006.01)
  *B01D 11/04*  (2006.01)
  *H01F 7/06*  (2006.01)
  *H01F 7/02*  (2006.01)
  *H02P 31/00*  (2006.01)
  *H01F 27/28*  (2006.01)
  *C12P 7/62*  (2006.01)
  *C12P 19/02*  (2006.01)
  *C12P 19/04*  (2006.01)
  *C12P 7/58*  (2006.01)
  *C12M 1/00*  (2006.01)

(52) U.S. Cl.
  CPC ............... *C12P 7/58* (2013.01); *C12P 7/62* (2013.01); *C12P 19/02* (2013.01); *C12P 19/04* (2013.01); *H01F 7/0205* (2013.01); *H01F 7/064* (2013.01); *H01F 27/2823* (2013.01); *H02P 31/00* (2013.01); *B01J 2219/0801* (2013.01); *B01J 2219/0854* (2013.01); *B01J 2219/0871* (2013.01); *C12M 29/18* (2013.01); *C12M 35/02* (2013.01); *C12M 35/06* (2013.01)

(56) References Cited

OTHER PUBLICATIONS

Office Action of corresponding CN application, published on Jan. 7, 2016.
Notice of Allowance of CN application, published on May 9, 2016.
Yang Na et al.; "Studies on the Inductive Methodology for Evaluating the Soluble Solid Content of Watermelon"; Modern Food Science and Technology; 2015, vol. 31, No. 3, pp. 249-254.
English Translation of Notice of Allowance of CN application, published on May 9, 2016.
International Search Report of international application PCT/CN2015/075098.

INDUCTIVE MAGNETOELECTRIC BIOCHEMICAL REACTION SYSTEM AND APPLICATION THEREOF

TECHNICAL FIELD

The present invention particularly relates to a multi-dimensionally controlled inductive magnetoelectric biochemical reaction system and applications thereof, for example, applications in the fields including assisted acid and enzyme hydrolysis, and modification of a natural polymer material, assisted extraction of a natural substance, and inducing and affecting a biochemical reaction.

BACKGROUND

A reactor is a system or device which is capable of providing suitable reaction conditions for chemical and biological reactions and converting a starting material into a specific product under a specific operation parameter, which is applied in chemical, biological and other light industry sections. Currently, liquid-phase reactors include tank reactors, hydrothermal synthesis reactors, vacuum reactors, photocatalytic reactors, microwave-chemical reactors, electrochemical reactors and the like. The controllable operation conditions of these reactors include temperature, pressure, vacuum degree, stirring speed, type of light source, light source power, microwave power, electrode shape, electrode area, voltage strength and the like. However, the control parameters of these reactors are relatively simple, and therefore magnetic fields and electric fields fail to be organically combined to achieve multi-dimensional control.

SUMMARY

A primary objective of the present invention is to provide an inductive magnetoelectric biochemical reaction system, which has abundant operation parameters.

Another objective of the present invention is to provide an application of the inductive magnetoelectric biochemical reaction system.

Still another objective of the present invention is to provide corresponding reaction methods.

To this end, the present invention employs the following technical solutions:

An inductive magnetoelectric biochemical reaction system is disclosed, comprising:

a reaction unit, comprising:

a reaction chamber, which comprises a reactant container and is located in a rotatable radial magnetic field;

a primary coil, which is wound around one side of a closed-loop iron core and is connected to a control unit;

a secondary coil, which is wound around the other side of the closed-loop iron core and comprises an insulating tube which allows a reaction solution acting as a secondary coil, two ends of the insulating tube being communicated with the reactant container;

a rotating magnetic field unit, which is configured to generate the rotatable radial magnetic field; and a control unit, which is at least configured to adjust a signal type with certain voltage level applied on the primary coil.

In an implementation solution, the control unit comprises a function signal generator, an output terminal of the function signal generator being connected to an input terminal of a power amplifier, an output terminal of the power amplifier being connected to the primary coil.

In an implementation solution, the function signal generator is capable of generating an AC signal having a frequency range of 50 to 200 Hz and a voltage level of 10 to 20 Vp-p, the AC signal comprising a sine wave, a triangular wave, a sawtooth wave, a unidirectional square wave, a bidirectional square wave, or a customized function signal.

In an implementation solution, the power amplifier has a power of 80 to 200 VA, an output AC voltage level of 200 to 400 Vp-p, and a full-power frequency width of 50 to 200 Hz.

In an implementation solution, the rotatable magnetic field unit comprises:

two arc permanent magnets which are fixedly arranged in an annular shape with heteropolars oppositely disposed, a radian of either of the two arc permanent magnets being less than 180 degrees; and a driving mechanism configured to drive the two arc permanent magnets to rotate.

Preferably, the arc permanent magnet has a central magnetic flux density of 2000 to 3000 Gs.

Further, the arc permanent magnet comprises but not limited to an NdFeB magnet.

In an implementation solution, the arc permanent magnet has a radian of 170 degrees.

Further, the rotatable magnetic field unit comprises a detachable iron yoke cylinder, the two arc permanent magnets are fixedly arranged in an annular shape on an inner wall of the iron yoke cylinder, and the iron yoke cylinder is connected to the driving mechanism based on transmission.

In an implementation solution, the driving mechanism comprises a servo motor controlled by a servo motor controller which is connected to the iron yoke cylinder.

More preferably, the reaction unit further comprises:

a temperature control unit, configured to control the temperature in the reactant container to −20 to 100° C.

In an implementation solution, the temperature control unit comprises a constant temperature circulating water bath which is connected with a water inlet and a water outlet of a jacket layer on the reaction chamber.

In an implementation solution, the primary coil is a single-strand copper wire having a diameter of 6 to 8 mm and having 20 to 26 turns.

In an implementation solution, the secondary coil comprises a glass spiral tube having an inner diameter of 2 to 3 mm, having 10 to 13 turns, and having a total length of 700 to 900 mm.

In an implementation solution, the closed-loop iron core is made of a silicon steel material and works in a frequency range of 50 to 200 Hz.

In an implementation solution, the secondary coil employs the glass spiral tube as a support tube of the reaction solution which is connected to two ends of the reactant container to form a communication state, a primary feeding port is arranged on an upper end of the reactant container, a secondary feeding port which is in perpendicular communication with the glass spiral tube is arranged on one side of the reactant container, and a glass jacket which allows circulating liquids at different temperatures to flow through is further arranged on the reaction chamber.

A biochemical reaction method is disclosed, comprising:

providing the inductive magnetoelectric biochemical reaction system as defined above; and pouring a reaction solution into the reaction unit, applying an AC excitation signal having a frequency of 50 to 200 Hz, a voltage level of 200 to 400 Vp-p and a power of 80 to 200 VA to the primary coil by using the control unit, and causing the rotatable radial magnetic field to rotate at a frequency of 0.1 to 50 Hz, wherein the rotatable radial magnetic field has a central magnetic flux density of 2000 to 3000 Gs.

Preferably, the reaction method further comprises: before or during the reaction, adjusting the temperature of the reactant container to a desired temperature.

Further, the biochemical reaction method further comprises: generating a sine wave, a triangular wave, a sawtooth wave, a unidirectional square wave, a bidirectional square wave or a customized function signal having a frequency of 50 to 200 Hz and a voltage level of 10 to 20 Vp-p by using a function signal generator, amplifying the signal by using a power amplifier having a power of 80 to 200 VA with a full-power frequency width of 50 to 200 Hz, causing an output AC signal to have a voltage level of 200 to 400 Vp-p, and exciting the primary coil using the output AC signal.

Also disclosed is an application of the inductive magnetoelectric biochemical reaction system as defined above or the biochemical reaction method as defined above for assisted acid hydrolysis, enzyme hydrolysis and modification of a natural polymer material, for assisted extraction of a natural compound, and for inducing and affecting a biochemical reaction.

Compared with the related art, the advantages of the present invention lie in that:

(1) The inductive magnetoelectric biochemical reaction system according to the present invention has more abundant operation conditions, including signal type, signal voltage level, signal frequency, strength of rotatable magnetic field, frequency of rotatable magnetic field, and the like.

(2) Based on the Faraday's law, the charged ions, charged compounds, charged particles, charged proteins or enzymes in the reaction solution are driven by the induced alternating electric field, and then various conductive effects are formed. Furthermore, in combination with the effect of the rotatable magnetic field and induced alternating electric field, the diffusion rate of these substances in the reaction solution is enhanced, and resulting in the changing of the reactive kinetic and the yield.

(3) Importantly, because the alternating electric field in the reaction solution is derived from the induced voltage, there is no need to use energized metal electrodes, which prevents occurrence of the adverse electrochemical reaction in the solution system.

Figure 1:
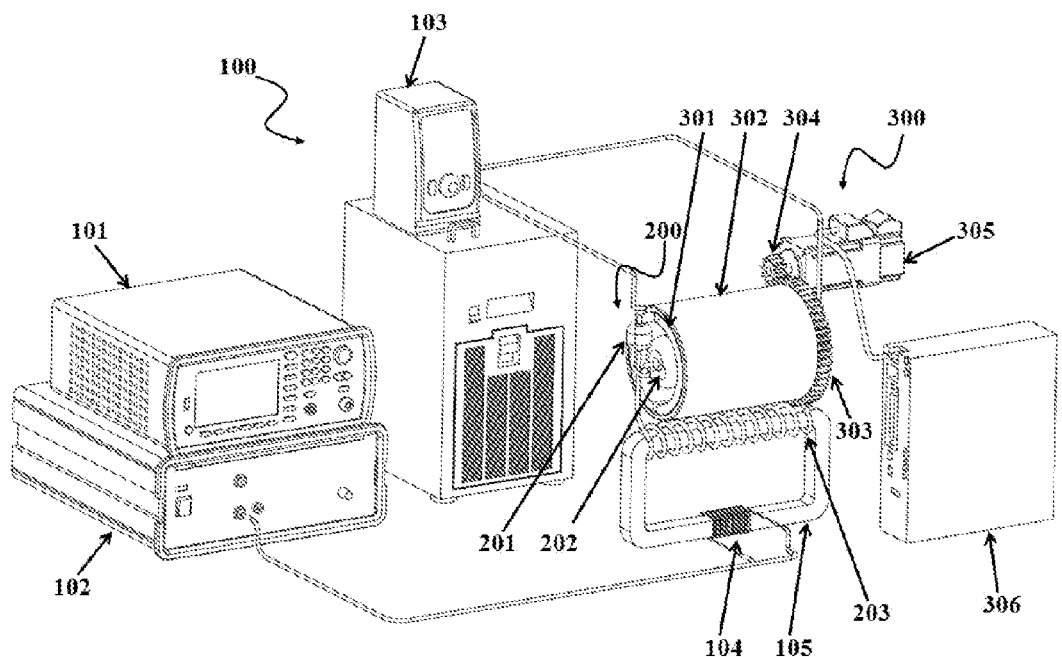
FIG. 1 is a schematic structural view of an inductive magnetoelectric biochemical reaction system according to an embodiment of the present invention.

Reference numerals and denotations thereof: 100—reaction system instrumental chain, 101—signal generator, 102—power amplifier, 103—constant temperature circulating water bath, 104—primary coil, 105—closed-loop iron core, 200—reaction unit, 201—secondary feeding port, 202—raction chamber, 203—glass spiral tube, 204—reactant container, 205—primary feeding port, 206—glass jacket, 207—jacket water inlet, 208—jacket water outlet, 300—rotating magnetic field unit, 301—two heteropolar-oppositely-disposed NdFeB arc permanent magnets with a radian of 170 degrees, 302—cylinder iron yoke, 303—iron yoke cylinder gear, 304—motor gear, 305—servo motor, 306—servo motor controller.

DETAILED DESCRIPTION

As described above, one aspect of the present invention provides an inductive magnetoelectric biochemical reaction system, which is capable of implementing multi-dimensional control of the operation parameters, including signal type, signal strength, signal frequency, strength of rotating magnetic field, frequency of rotating magnetic field, and the like.

In an implementation solution of the present invention, the inductive magnetoelectric biochemical reaction system may comprise a closed-loop iron core, a primary coil, a glass spiral tube serving as a support tube of the reaction solution in a secondary coil, a reaction chamber, a control unit, a rotating magnetic field unit, and the like.

According to the Faraday's law, the reaction system works based on an O-core transformer structure: the secondary coil winding on the closed-loop iron core is subjected to an excitation voltage having different waveforms, frequencies and levels, then the corresponding alternating magnetic flux is generated in the closed-loop iron core, and thus the induced alternating electric field appears in reaction solution which also acts as the secondary coil. Both ends of the reactant container are in communication with the secondary coil solution. In the mean time, the biochemical substances in the reaction chamber are also subjected to the treatment of the rotatable magnetic field. Therefore, charged ions, charged particles, charged organic compounds and charged proteins as well as charged enzymes in the reaction solution are affected by both induced alternating electric field and rotatable magnetic field. This enhances the conductive effect of the reaction solution, and then the diffusion rate of these substances in the reaction solution is affected, and resulting in the changing of the reactive kinetic and the yield.

To be specific, with respect to the working process of the transformer, if an alternating excitation voltage $U_p$ is applied to a primary coil ($N_p$), a magnetic flux in compliance with the corresponding variation rule, wherein the value of the magnetic flux is in positive proportion to the number of turns of the coil, which is represented by equation (1):

$$U_p = -N_p \frac{d\phi}{dt} \quad (1)$$

In formula (1), $U_p$ denotes an excited voltage, $N_p$ denotes the number of turns of the primary coil, $d\phi$ denotes a magnetic flux differential, and $dt$ denotes a time differential.

Ampere's Law states that the line integral of the magnetic field intensity around a closed contour is equal to the total current enclosed, which is represented by equation (2).

$$\oint \vec{H} \cdot \vec{dl} = i \quad (2)$$

In the case where there are a discrete number of loops, as in the case of a closed transformer core multi-turn coil, equation (2) becomes:

$$\sum_N H \cdot l = Ni \quad (3)$$

In the above equations, H denotes a magnetic field strength, l denotes a length of the closed-loop magnetic circuit, i denotes a current in the closed-loop circuit, and N denotes the number of turns of the coil.

The alternating magnetic flux in the iron core magnetic circuit would generate an induced voltage $E_s$ in compliant variation rule in the secondary coil ($N_s$), which is represented by equation (4):

$$E_s = -N_s \frac{d\phi}{dt} \quad (4)$$

In equation (4), $E_s$ denotes an induced voltage, $N_s$ denotes the number of turns of the secondary coil, $d\phi$ denotes a magnetic flux differential, and $dt$ denotes a time differential.

As known from equation (1) and (4), $$E_p/E_s = U_p/U_s = N_p/N_s \quad (5)$$

As known from equation (5), $U_P$ is the excitation voltage on the primary coil, $E_P$ is the induced voltage in the primary coil, $U_S$ is the terminal voltage on the secondary coil, $E_S$ is the induced voltage in the secondary coil, $N_P$ is the primary coil turns, and $N_S$ is the secondary coil turns respectively. Provided that the excitation voltage and the ratio of the number of turns of the primary coil to the number of turns of the secondary coil are fixed, then the induced voltage is a fixed value.

In the reaction system according to the present invention, since internal impedance exists in the secondary coil, the induced voltage $E_s$ of the secondary circuit is applied to both external load and coil impedance. If an electro-conductive solution is used as the conductor of the secondary coil, under the effect of the alternating magnetic flux, according to the Ampere circuital theorem, the induced alternating electric field is likewise obtained in the reaction solution.

The reaction system containing the biomechanical solution contains a large amount of charged ions, charged compounds, charged particles as well as charged proteins and enzymes, which experience oriented motion under the effect of the electric field force ($F_E$), and the electric field force is equal to the product of the net charge quantity (q) and the electric field strength (E), that is, $F_E = qE$. The moving charged ions, electrically charged compounds, charged particles, charged proteins and enzymes will be affected by a perpendicular magnetic field. Under the effect of the Lorentz force ($F_M$), the motion trajectory of the substances would deviate. The Lorentz force $F_M = qvB$, wherein v denotes a motion speed of the substances, q denotes a static charge quantity carried by the substances, and B denotes a component of the perpendicular magnetic field. In addition, the alternating magnetic field is capable of generating a tiny induced current in a electro-conductive solution, which breaks an association structure of the water molecules in the liquid and changes large associated water clusters into small ones, even a single water molecule. As such, the viscosity of the solution is reduced. This is because the combination is not as strong as chemical bonds when the water molecules are associated via hydrogen bonds. Therefore, the water molecules are always in a dynamic equilibrium where they are constantly disconnected from and combined with each other, which is represented by equation (6):

$$(H_2O)_n = xH_2O + (H_2O)_{n-x} \quad (6)$$

Under certain conditions, the energy needed in the dynamic equilibrium is provided by the thermal motion of water molecules. The alternating magnetic field inevitably provides energy for the thermal motion of water molecules in the reaction system, which facilitates the dynamic balance to move towards the direction in which the water cluster is opened. As a result, the hydrogen bonds between some water molecules break and the water molecule activity in the solution is enhanced, i.e., the available effective water molecules in the biochemical reaction system increase.

Generally, the chemical reaction rate in the sample solution is closely related to the activation energy. When the temperature rises, the activation energy is reduced. With lower activation energy, the reaction rate is higher. When the alternating electric field and the alternating magnetic field are not applied, the charged solutes and water molecules in the solution system move irregularly. When the alternating electric field and the alternating magnetic field are applied at the same time and their directions are vertical to each other theoretically, the charged ions, charged compounds, charged particles, charged proteins and enzymes in the solution system may be affected by both the periodic electric field force and the magnetic field force, and thus large-scale orientated motions may occur.

Therefore, applying the alternating electric field and the alternating magnetic field on the reaction solution may cause the orientation movement of the charged solutes, which ultimately changes the diffusion and mass transfer in the reaction solution, thereby affecting the reactive kinetic and the yield.

In conclusion, in the present invention, based on the inductive methodology, the primary coil is excited by various types of signals to produce an alternating magnetic flux to affect the reaction solution, an electro-conductive medium, and trigger the oriented motion of free ions, charged particles or charged organic compounds and charged proteins and enzymes in the solution system, simultaneously in combination with the effect of the rotatable magnetic field. As such, the operation parameters of such a biochemical reaction system are abundant compared with a traditional batch reaction system.

Based on the principle as mentioned above, in an implementation solution of the present invention, i.e., in the inductive magnetoelectric biochemical reaction system, the reaction solution acts as the secondary coil fulfilled with a glass spiral tube. When a signal generated by the function signal generator excites the primary coil after being amplified by the power amplifier, an alternating magnetic flux at the corresponding frequency is generated in the closed-loop iron core, and an induced alternating voltage may be obtained in the secondary coil, i.e., that is an induced alternating electric field appears in the reaction solution. Meanwhile, a rotatable perpendicular magnetic field is arranged on an outer side of the reaction chamber, and a jacket structure is also arranged in the reaction chamber, which may be in communication with circulating liquids at different temperatures via constant temperature water bath. In this way, the effect of controlling the temperature of the reaction system is achieved.

The detailed work of the reaction system is as follows: The function signal generator generates a sine wave, a triangular wave, a sawtooth wave, a unidirectional square wave, a bi-directional square wave or a customized function signal having a frequency of 50 to 200 Hz, wherein the above AC signal has a voltage level of 10 to 20 V-pp; then the power amplifier having a power of 80 to 200 VA and a full-power frequency width of 50 to 200 Hz amplifies the signal such that an output voltage level is 200 to 400 Vp-p; the amplified signal excites the primary coil; the windings of the primary coil are wound around one side of the closed-loop iron core which works at a frequency of 50 to 200 Hz; the sample solution in the reaction system is used as the conductor of the secondary coil and is in communication with the reactant container; in this case, induced alternating electric field in compliance with different variation rules appears in the reaction solution; a rotatable radial magnetic field is formed on an outer side of the reaction chamber, with a magnetic flux density of 2000 to 3000 Gs and a rotation frequency of 0.1 to 50 Hz; and the temperature of the reaction system may be controlled to −20 to 100° C.

In an embodiment, the support tube of the reaction solution in the secondary coil is made of an insulating glass material, which is intended to reduce power loss of the secondary coil.

In an embodiment, the primary coil may be a single-strand copper wire, having a diameter of 6 to 8 mm and having 20 to 26 turns.

In an embodiment, the support tube of the secondary reaction solution is a glass spiral tube, having an inner diameter of 2 to 3 mm, 10 to 13 turns and a total length of 700 to 900 mm.

In an embodiment, the reaction chamber has an inner diameter of 20 to 25 mm and a length of 130 mm. A primary feeding port is arranged on an upper end of the reactant container, a secondary feeding port which is in vertical communication with the glass spiral tube is arranged on one side of the reactant container, and a glass jacket which allows circulating liquids with different temperatures to flow through to control the reaction temperature is arranged outside the reactant container. The overall height of the reaction chamber including the main feeding port does not exceed 80 mm.

In an embodiment, the temperature of the reaction system is maintained by a constant temperature circulating water bath which is in communication with the outlet and inlet of the jacketed layer on the reaction chamber.

In an embodiment, a rotatable perpendicular magnetic field is formed by two heteropolar-oppositely-disposed NdFeB arc permanent magnets with a radian of 170 degrees, i.e., the N pole of one arc permanent magnet is opposite to the S pole of the other arc permanent magnet, and the arc NdFeB permanent magnet has a length 130 mm, with an outer diameter of 80 mm, an inner diameter of 65 mm, a thickness of 15 mm and a central magnetic flux density of 2000 to 3000 Gs. The iron yoke cylinder close to the outer side of the two NdFeB arc permanent magnets is fixedly arranged and is detachable. The iron yoke cylinder is driven to rotate at a constant speed through the gear driven by the servo motor. The servo motor is controlled by a servo motor controller.

Obviously, technicians in this field can also adjust the size and structure, etc. of any components mentioned above according to this instruction and combined with the common sense in this field as well as practical application demands.

Another aspect of the present invention provides a biochemical reaction method using the inductive magnetoelectric biochemical reaction system. The method comprises:

providing the inductive magnetoelectric biochemical reaction system as defined above; and pouring a reaction solution into the reaction unit, applying an AC excitation signal having a frequency of 50 to 200 Hz and a voltage level of 200 to 400 Vp-p to the primary coil by using the control unit, and causing the rotatable perpendicular magnetic field to rotate at a frequency of 0.1 to 50 Hz, wherein the rotatable radial magnetic field has a central magnetic flux density of 2000 to 3000 Gs.

Still another aspect of the present invention provides application of the inductive magnetoelectric biochemical reaction system, wherein the application includes: assisted acid hydrolysis, enzyme hydrolysis and modification of a natural polymer material, assisted extraction of a natural compound, and affecting reactive kinetic, which are not limited thereto.

The inductive magnetoelectric biochemical reaction system according to the present invention has more abundant operation conditions, including signal type, signal voltage level, signal frequency, intensity of rotatable magnetic field, frequency of rotatable magnetic field, and the like. In addition to a sine wave, a sawtooth wave, a triangular wave, a single-phase square wave and a bidirectional square wave, a customized asymmetric periodic signal is also included.

If asymmetric periodic waveform is applied on the primary coil, alternating magnetic flux with corresponding frequency will be produced in the closed-loop iron core, which lead to the induced voltage of asymmetric waveform appeared in the sample solution which acted as the secondary coil. Further, it will have a specific driven effect on charged ions, charged compounds, charged particles, charged proteins and enzymes owing to the alternating electric field force combined with magnetic field force.

In general, regardless of whether a signal of regular periodic waveform, such as sine wave, sawtooth wave, triangular wave, unidirectional square wave, bidirectional square wave, and even customized asymmetric periodic signal is used to excite the primary coil to obtain induced alternating electric field to drive the charged ions, charged compounds, charged particles, charged proteins or enzymes in the sample solution, specific mass transfer and conductive effects may be achieved. In combination with the effect of the rotatable magnetic field, the diffusion rate of the substances in the reaction solution is changing, and the progress of the biochemical reaction is affected.

Importantly, since the induced alternating electric field in the reaction solution is derived from inductive methodology, there is no need to use energized metal electrodes, which prevents occurrence of adverse electrochemical reaction in the sample solution.

The technical solution of the present invention is further interpreted and described with reference to several embodiments and the attached drawings.

Embodiment 1

Hereinafter, using the preparation of hydroxypropylated glutinous rice starch based on the alkali method as an example, application of the inductive magnetoelectric biochemical reaction system in the assisted modification of a natural polymer material is further described.

As illustrated in FIG. 1 to FIG. 4, in this embodiment, the present invention provides an inductive magnetoelectric biochemical reaction system, comprising a reaction system instrumental chain 100, a reaction unit 200, and a rotatable magnetic field unit 300.

Figure 2:
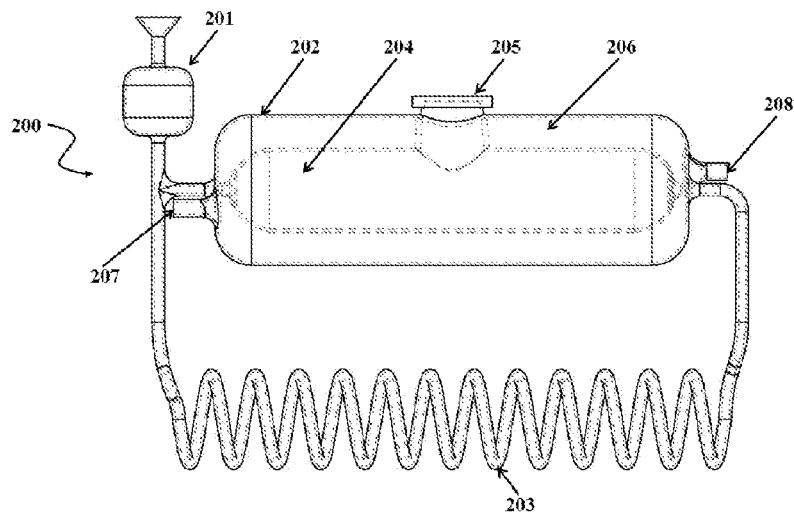
FIG. 2 is a sectional view of a reaction chamber according to an embodiment of the present invention.
Figure 3A:
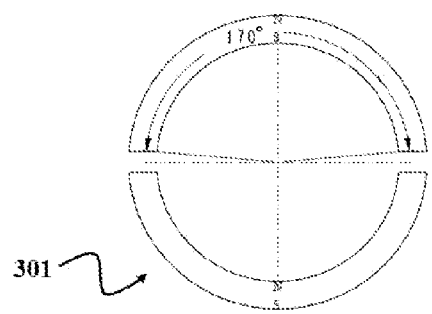
FIG. 3a, FIG. 3b and FIG. 3c are a front view, a side view and a three-dimensional diagram of two opposite arc NdFeB magnets according to an embodiment of the present invention.
Figure 3B:
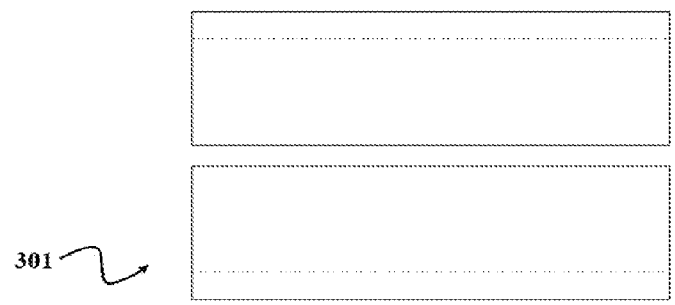
Figure 3C:
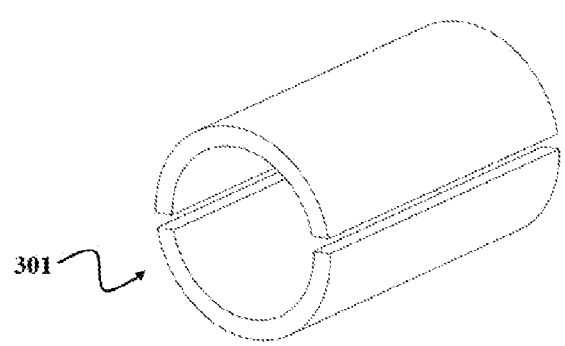
Figure 4:
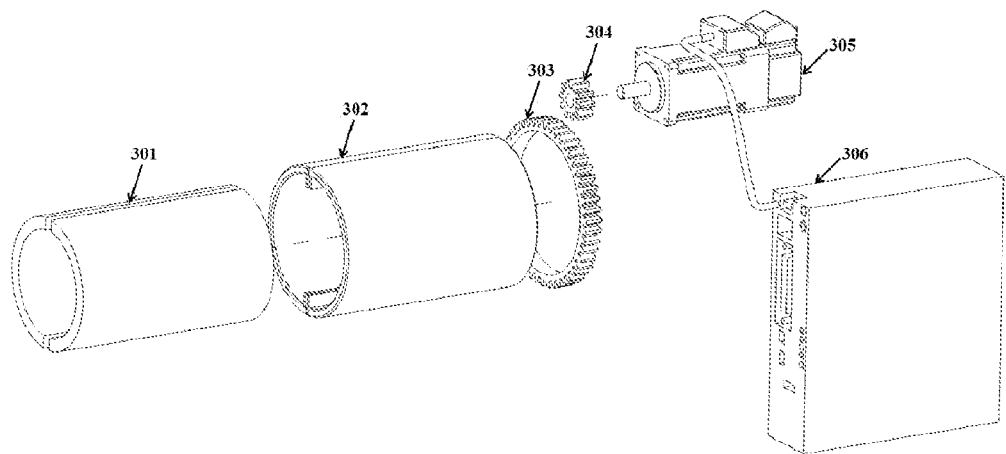
FIG. 4 is a schematic structural view of a rotating magnetic field unit according to an embodiment of the present invention.

Referring to FIG. 1, the reaction system instrumental chain 100 comprises a signal generator 101, a power amplifier 102, a constant temperature circulating water bath 103, a reaction unit 200, a secondary feeding port 201 included in the reaction unit 200, a reaction chamber 202 including a glass spiral tube spiral tube 203, a rotatable magnetic field unit 300, two heteropolar-oppositely-disposed NdFeB arc permanent magnets 301 with a radian of 170 degrees, a cylinder iron yoke 302 supporting the arc permanent magnet, an iron yoke cylinder gear 303, a motor gear 304, a servo motor 305, and a servo motor controller 306. An output terminal of the function signal generator 101 is connected to an input terminal of the power amplifier 102. An output terminal of the power amplifier 102 is connected to the primary coil 104. The used function signal generator 101 is capable of generating an AC signal having a frequency range of 50 to 200 Hz and a voltage level of 10 to 20 Vp-p, wherein the AC signal comprises a sine wave, a triangular wave, a sawtooth wave, a unidirectional square wave, a bidirectional square wave, or a customized function signal. The used power amplifier 102 has an output power range of 80 to 200 VA and a full-power frequency width of 50 to 200 Hz, wherein after the signal is amplified by the power amplifier 102 20 times, an output AC voltage level ranges from 200 to 400 Vp-p. The primary coil 104 is a single-strand copper wire having a diameter of 6 mm and having 26 turns. Meanwhile, the primary coil 104 is wound around one side of the closed-loop iron core 105, and the closed-loop iron core 105 is made of a silicon steel material and works at a frequency of 50 to 200 Hz, wherein the closed loop has a central circumference of 520 mm and a height of 15 mm. The glass spiral tube 203 on the reaction chamber 202 is arranged on the other side of the closed-loop iron core 105, wherein the glass spiral tube 203 has an inner diameter of 3 mm, having 13 turns and a total length of 856 mm. FIG. 2 is a schematic sectional view of a main body of the reaction unit 200. Both ends of the glass spiral tube 203 are connected to the reactant container 204 to form a communication state. The reactant container 204 in the reaction chamber 202 has an inner diameter of 25 mm and a length of 130 mm. A primary feeding port 205 is arranged on an upper end of the reaction container, wherein the primary feeding port 205 has a diameter of 25 mm. A secondary feeding port 201 in vertical communication with the glass spiral tube 203 is arranged on one side of the reactant container 204, and a glass jacket 206 which allows circulating liquids with different temperatures to flow through to keep the reaction temperature is arranged outside the reactant container 204. The overall height of a jacket water inlet 207, a jacket water outlet 208, and the primary feeding port 205 included in the reaction chamber 202 does not exceed 60 mm. A rotatable perpendicular magnetic field is formed on the outer side of the reaction chamber 202 which includes the primary feeding port 205, wherein the perpendicular magnetic field thereof is formed by two heteropolar-oppositely-disposed NdFeB arc permanent magnets with a radian of 170 degrees, i.e., the N pole of one arc permanent magnet is opposite to the S pole of the other arc permanent magnet. The NdFeB arc permanent magnet has a length of 130 mm, an outer diameter of 80 mm, an inner diameter of 65 mm and a thickness of 15 mm. As illustrated in FIG. 3, the arc permanent magnet has a central magnetic flux density of 2200 Gs. An iron yoke cylinder 302 close to the outer side of the two NdFeB arc permanent magnets is fixedly arranged and is detachable. The servo motor 305 drives the motor gear 304 and the iron yoke cylinder gear 303 to finally drive the iron yoke cylinder 302 to rotate at a constant speed. The servo motor 305 is controlled by the servo motor controller 306, with a rotation frequency of 0.1 to 50 Hz. The rotatable magnetic field unit is as illustrated in FIG. 4. For temperature control in the reaction system, the constant temperature circulating water bath 103 is in communication with the water inlet 207 and the water outlet 208 on the circulating water jacket 206 in the reaction chamber 202, with a temperature range of −20 to 100° C.

Figure 5:
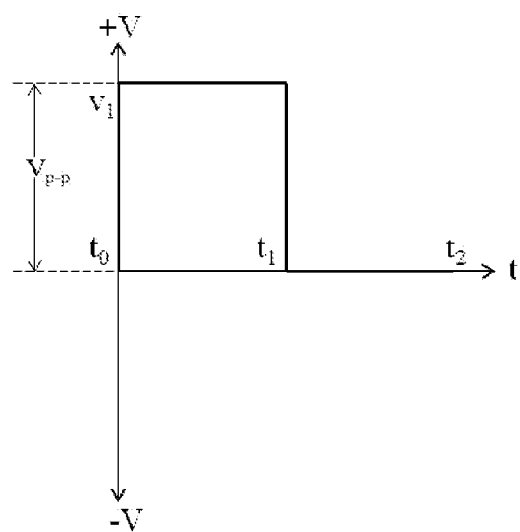
FIG. 5 is a waveform graph of a unidirectional square wave employed in the assisted preparation of hydroxypropylated glutinous rice starch according to an embodiment of the present invention.

The preparation of the hydroxypropylated glutinous rice starch performed by using the reaction system comprises the following steps:

Step 1: taking 13 g of glutinous rice starch into a breaker, adding 40 g of distilled water, mixing and shaking uniformly to obtain a starch emulsion, stirring the emulsion at 40° C. for 15 minutes, slowly adding 0.95 g of anhydrous sodium sulfate, stirring for another 5 minutes, adding 5 ml of NaOH solution having a concentration of 1 mol/L, and stirring for 3 minutes;

Step 2: pouring the starch emulsion from the secondary feeding port 201 to immerse the glass spiral tube 203, and when the emulsion enters the reactant container 204, placing 0.8 g of epoxy propane into the reactant container 204 from the primary feeding port 205, and stirring the resulted emulsion uniformly;

Step 3: enabling the signal generator 101 and choosing the unidirectional square wave, and setting the voltage and the cycle as illustrated in FIG. 5, wherein $t_0$=0 s, $t_1$=0.005 s, $t_2$=0.01 s, the signal cycle is 0.01 s, that is, a frequency of 100 Hz, $v_1$=10 V, the signal voltage level $V_{p-p}$=10 V, enabling the power amplifier 102 to amplify the unidirectional square wave signal by 20 times, and exciting the primary coil 104 wound on the closed-loop iron core 105, such that an induced alternating electric field is generated in the solution in the reactant container 204; meanwhile, regulating the servo motor controller 306 to control its speed at 20 Hz, such that, a rotatable magnetic field is generated, that is, two heteropolar-oppositely-disposed NdFeB arc permanent magnets with a radian of 170 degrees rotate;

Step 4: turning on the constant temperature circulating water bath 103 such that the 45° C. circulating water enters from the water inlet 207 of the glass jacket 206, and then flows out from the water outlet 208;

Step 5: maintaining the above state for 16 hours, then disabling the signal generator 101, the power amplifier 102, the servo motor controller 306 and the constant temperature circulating water bath 103, discharging the mixed solution from the reactant container 204 and pouring the solution to a the breaker, immediately adding a HCl solution having a mass ratio of 1% such that the pH value of the mixed solution is equal to 6.5, terminating the reaction, filtering, washing and drying the reaction product at an oven at 55° C. for 6 hours, and finally crushing the product and subjecting the product to a 120-mesh sieve to obtain the hydroxypropylated glutinous rice starch.

Upon test, the substitution degree of the hydroxypropylated glutinous rice starch obtained by using the inductive magnetoelectric biochemical reaction system is 0.12. As compared with this, if the other reaction conditions are the same, but the induced alternating electric field and the rotatable magnetic field are not applied, i.e., only the above reaction solution is maintained in the reactant container 204 at 45° C. for 16 hours, then the substitution degree of the finally resulted hydroxypropylated glutinous rice starch is only 0.05.

Embodiment 2

The application of the reaction system is further described by using the inductive magnetoelectric biochemical reaction system according to Embodiment 1, and using the assisted enzyme hydrolysis of a natural polymer material as an example.

Figure 6:
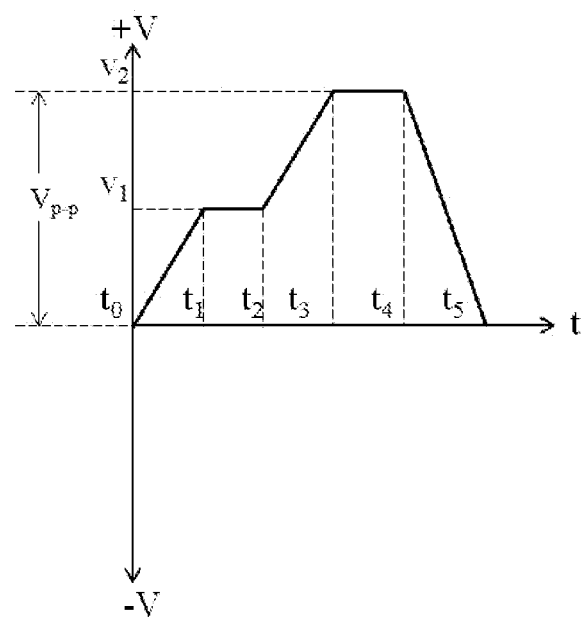
FIG. 6 is a waveform graph of a customized wave employed in the assisted preparation of enzymolytically modified corn starch according to an embodiment of the present invention.

The preparation of oil absorbent corn starch using assisted enzyme hydrolysis of corn starch by using the reaction system comprises the following steps:

Step 1: taking 15 g of corn starch into a breaker, adding 50 g of distilled water, mixing and shaking uniformly to obtain a starch emulsion, adding a disodium hydrogen phosphate-citrate buffer having a concentration of 1 mol/L, regulating the pH value of the starch emulsion to 4.0, and stirring at 40 for 15 minutes;

Step 2: pouring the starch emulsion having the pH of 4 from the secondary feeding port 201 to immerse the glass spiral tube 203, and when the emulsion enters the reactant container 204, placing 0.3 g of saccharifying enzyme powder having a enzyme activity of 100000 units into the reactant container 204 from the primary feeding port 205;

Step 3: enabling the signal generator 101, choosing the customized signal, and setting the voltage and the cycle as illustrated in FIG. 6, wherein $t_0=0$ s, $t_1=0.0025$, $t_2=0.0045$, $t_3=0.0065$, $t_4=0.0085$, $t_5=0.01$ s, the signal cycle is 0.01 s, that is, a frequency of 100 Hz, $v_1=10$ V, $v_2=10$ V, the signal voltage level $V_{p-p}=10$ V, enabling the power amplifier 102 to amplify the customized signal by 20 times, and exciting the primary coil 104 wound on the closed-loop iron core 105, such that an induced alternating electric field is generated in the sample solution in the reactant container 204; meanwhile, regulating the servo motor controller 306 to control its speed at 10 Hz, such that a rotatable magnetic field is generated, that is, two heteropolar-oppositely-disposed NdFeB arc permanent magnets with a radian of 170 degrees rotate;

Step 4: turning on the constant temperature circulating water bath 103 such that the 62° C. circulating water enters from the water inlet 207 of the glass jacket 206, and then flows out from the water outlet 208;

Step 5: maintaining the above state for 4 hours, then disabling the signal generator 101, the power amplifier 102, the servo motor controller 306 and the constant temperature circulating water bath 103, discharging the mixed solution from the reactant container 204 and pouring the solution to a the breaker, immediately adding a NaOH solution having a mass ratio of 4% such that the pH value of the mixed solution is equal to 7, terminating the enzyme reaction, centrifuging the starch emulsion at 3000 r/min for 15 minutes and precipitating the starch emulsion, drying the precipitate in a oven at 55° C. for 3 hours, crushing the precipitate and subjecting the crushed precipitate to a 200-mesh sieve, to obtain a modified oil absorbent corn starch.

Upon test, the oil absorbent rate of the modified corn starch obtained via enzyme hydrolysis by using the inductive magnetoelectric biochemical reaction system is 142%. As compared with this, the oil absorbent rate of the original corn starch that is subjected to no treatment is only 24%. If the above corn starch emulsion having the regulated pH value and being preheated is maintained in the reactant container 204, and likewise the emulsion is kept at 62° C. for 4 hours, i.e., the induced alternating electric field and the rotatable magnetic field are not applied, then the oil absorbent rate of the corn starch obtained via enzyme hydrolysis is only 85%.

Embodiment 3

The application of the reaction system is further described by using the inductive magnetoelectric biochemical reaction system according to Embodiment 1, and using the assisted acid hydrolysis of a natural polymer material as an example.

Figure 7:
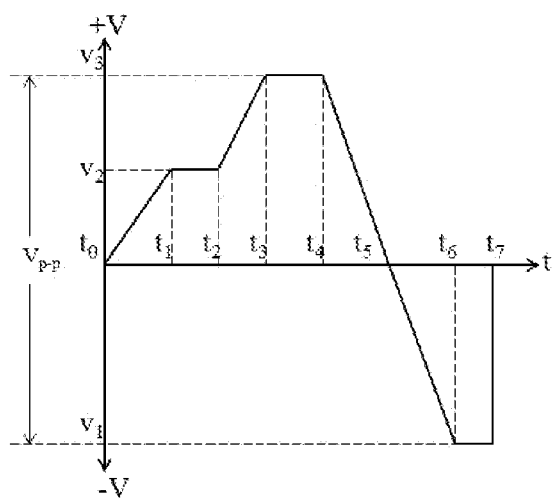
FIG. 7 is a waveform graph of a customized wave employed in the assisted acid hydrolysis of cellulose according to an embodiment of the present invention.

The preparation of reducing sugar using assisted hydrochloric acid hydrolysis of cellulose by using the reaction system comprises the following steps:

Step 1: taking 0.5 g of cellulose powder into a breaker, adding 5 g of distilled water, mixing and shaking uniformly, adding 8 mL of hydrochloric acid solution having a concentration of 36%, and stirring the solution uniformly;

Step 2: pouring the reactants from the secondary feeding port 201 to immerse the glass spiral tube 203 such that the reactants enter the reactant container 204;

Step 3: enabling the signal generator 101 and choosing the customized signal, and setting the voltage and the cycle as illustrated in FIG. 7, wherein $t_0=0$ s, $t_1=0.003$ s, $t_2=0.0065$, $t_3=0.0095$, $t_4=0.011$ s, $t_5=0.018$ s, $t_7=0.02$ s, the signal cycle is 0.02 s, that is, a frequency of 50 Hz, $v_1=-10$ V, $v_2=5$ V, $v_3=10$ V, the signal voltage level $V_{p-p}=20$ V, enabling the power amplifier 102 to amplify the customized signal by 20 times, and exciting the primary coil 104 wound on the closed-loop iron core 105, such that an induced alternating electric field is generated in the sample solution in the reactant container 204; meanwhile, regulating the servo motor controller 306 to control its speed at 10 Hz, such that a rotatable magnetic field is generated, that is, two heteropolar-oppositely-disposed NdFeB arc permanent magnets with a radian of 170 degrees rotate.

Step 4: turning on the constant temperature circulating water bath 103 such that the 80° C. circulating water enters from the water inlet 207 of the glass jacket 206, and then flows out from the water outlet 208;

Step 5: keeping the above state for 12 hours, disabling the signal generator 101, the power amplifier 102, the servo motor controller 306 and the constant temperature circulating water bath 103, discharging the mixed solution from the reactant container 204 and pouring the solution to the breaker, immediately adding a NaOH solution having a mass ratio of 1% to regulate the pH of the mixed solution to 7, and then suction filtering the mixed solution to obtain a filtrate containing the reducing sugar.

Upon test, the content of the reducing sugar in the cellulose filtrate obtained via acid hydrolysis by using the inductive magnetoelectric biochemical reaction system is 58.4 mg/L. As compared with this, if the other reaction conditions are the same, and the induced alternating electric field and the rotatable magnetic field are not applied, that is, the cellulose-hydrochloric acid mixed solution is only maintained in the reactant container 204 at 80° C. for 12 hours, then the content of the reducing sugar in the cellulose filtrate finally resulted via acid hydrolysis is 12.5 mg/L.

Embodiment 4

The application of the reaction system is further described by using the inductive magnetoelectric biochemical reaction system according to Embodiment 1, and using the assisted extraction a natural product as an example.

Figure 8:
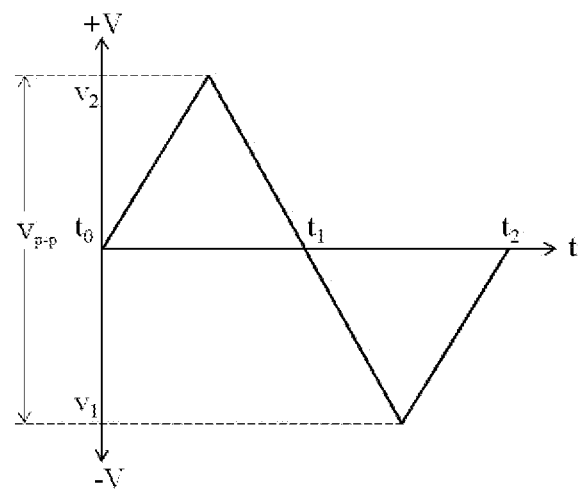
FIG. 8 is a waveform graph of a triangular wave employed in the assisted extraction of pectin from apple pomace according to an embodiment of the present invention.

The assisted extraction of pectin, i.e., galacturonic acid, from apple pomace by using the inductive magnetoelectric biochemical reaction system comprises the following steps:

Step 1: weighing 18 g of apple pomace having a water content of 40%, washing and suction filtering the apple pomace with 200 mL of 35° C. distilled water to remove soluble sugars and pigment, and then injecting the apple pomace experiencing the suction filtration into the reactant container 204 from the primary feeding port 205;

Step 3: at room temperature, injecting 50 g of distilled water from the secondary feeding port 201 to immerse glass spiral tube 203 until the apple pomace in the reactant container 204 has been immersed, adding HCl having a concentration of 1 mol/L into the reactant container 204 from the primary feeding port 205, and regulating the pH value of the reaction system to 3;

Step 3: enabling the signal generator 101 and choosing the triangular wave signal, and setting the voltage and the cycle as illustrated in FIG. 8, wherein $t_0=0$ s, $t_1=0.005$ s, $t_2=0.01$ s, the signal cycle is 0.01 s, that is, a frequency of 100 Hz, $v_1=-5$ V, $v_2=5$ V, the signal voltage level $V_{p-p}=10$ V, enabling the power amplifier 102 to amplify the unidirectional square wave signal by 20 times, and exciting the primary coil 104 on the closed-loop iron core 105, such that an induced alternating electric field is generated in the sample solution in the reactant container 204; meanwhile, regulating the servo motor controller 306 to control its speed at 10 Hz, such that a rotatable magnetic field is generated, that is, two heteropolar-oppositely-disposed NdFeB arc permanent magnets with a radian of 170 degrees rotate.

Step 4: turning on the constant temperature circulating water bath 103 such that the 50° C. circulating water enters from the water inlet 207 of the glass jacket 206, and then flows out from the water outlet 208;

Step 5: keeping the above state for 60 minutes, disabling the signal generator 101, the power amplifier 102, the servo motor controller 306 and the constant temperature circulating water bath 103, discharging the feed liquid of the apple pomace from the reactant container 204, centrifuging the feed liquid at 5000 r/min for 5 minutes, and separating the precipitate of the apple pomace to obtain a supernatant.

Upon test, the content of the galacturonic acid in the supernatant obtained via treatment of the apple pomace by using the inductive magnetoelectric biochemical reaction system is 13.6 wt %. As compared with this, if the apple pomace is only soaked according to the above feed liquid ratio and pH value and maintained in the reactant container 204 and soaked at 50° C. for 60 minutes, i.e., the induced alternating electric field and the rotatable magnetic field are not applied, then the supernatant resulted via precipitation of the feed liquid of the apple pomace, the content of galacturonic acid is 7.4 wt %.

Embodiment 5

The application of the reaction system is further described by using the inductive magnetoelectric biochemical reaction system according to Embodiment 1, and using the inducing and affecting of a biochemical reaction as an example.

Figure 9:
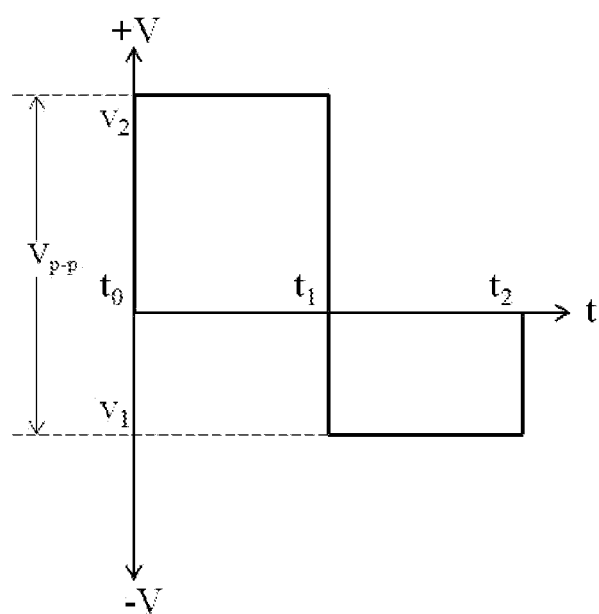
FIG. 9 is a waveform graph of a customized wave employed in an ethanol-latic acid emulsification reaction according to an embodiment of the present invention.

The preparation of ethyl lactate by assisted synthesis through lactic acid and ethanol by using the inductive magnetoelectric biochemical reaction system comprises the following steps:

Step 1: taking 180 g of lactic acid into a volumetric flask, adding 50.8 g of distilled water, mixing and shaking to obtain a lactic acid aqueous solution having a concentration of 10 mol/L, taking 92 g of anhydrous ethanol into the volumetric flask, adding 83.5 g of distilled water, mixing and shaking to obtain an ethanol aqueous solution having a concentration of 10 mol/L;

Step 2: mixing 32 mL of lactic acid aqueous solution having a concentration of 10 mol/L and 32 mL ethanol aqueous solution having a concentration of 10 mol/L, and injecting the solution from the secondary feeding port 201 to immerse the glass spiral tube 203, such that the solution enters the reactant container 204;

Step 3: enabling the signal generator 101 and choosing the triangular wave signal, and setting the voltage and the cycle as illustrated in FIG. 9, wherein $t_0=0$ s, $t_1=0.01$ s, $t_2=0.02$ s, the signal cycle is 0.02 s, that is, a frequency of 50 Hz, $v_1=-3$V, $v_2=7$ V, the signal voltage level $V_{p-p}=10$ V, enabling the power amplifier 102 to amplify the unidirectional square wave signal by 20 times, and exciting the primary coil 104 on the closed-loop iron core 105, such that an induced alternating electric field is generated in the reactant container 204; meanwhile, regulating the servo motor controller 306 to control its t rotation speed at 5 Hz, such that a rotatable magnetic field is generated, that is, two heteropolar-oppositely-disposed NdFeB arc permanent magnets with a radian of 170 degrees rotate.

Step 4: turning on the constant temperature circulating water bath 103 such that the 40° C. circulating water enters from the water inlet 207 of the glass jacket 206, and then flows out from the water outlet 208;

Step 5: keeping the above state for 10 hours, disabling the signal generator 101, the power amplifier 102, the servo motor controller 306 and the constant temperature circulating water bath 103, discharging the mixed solution from the reactant container 204.

Upon test, the content of the ethyl lactate in the mixed solution obtained via treatment by using the inductive magnetoelectric biochemical reaction system is 0.19 mol/L. As compared with this, if 32 mL of lactic acid aqueous solution having a concentration of 10 mol/L and 32 mL of ethanol aqueous solution having a concentration of 10 mol/L are only mixed and then maintained in the reactant container 204 at 30 for 10 hours, i.e., the induced alternating electric field and the rotatable magnetic field are not applied, then the content of the ethyl lactate in the mixed solution is only 0.07 mol/L.

It should be noted that, in this specification, terms "comprises", "comprising", "has", "having", "includes", "including", "contains", "containing" or any other variation thereof, are intended to cover a non-exclusive inclusion, such that a process, method, article, or apparatus, that comprises, has, includes, contains a list of elements does not include only those elements but may include other elements not expressly listed or inherent to such process, method, article, or apparatus.

Described above are specific embodiments of the present invention. It should be noted that persons of ordinary skill in the art may derive other improvements or polishments without departing from the principles of the present inven-

What is claimed is:

1. An inductive magnetoelectric biochemical reaction system, comprising:
   a reaction unit, comprising:
   a reaction chamber, which comprises a reactant container and is disposed in a rotatable radial magnetic field;
   a primary coil, which is wound around one side of a closed-loop iron core and is connected to a control unit;
   a secondary coil, which is wound around the other side of the closed-loop iron core and comprises an insulating tube which allows a reaction solution acting as a conductor, two ends of the insulating tube being communicated with the reactant container;
   a rotatable magnetic field unit, which is configured to generate the rotatable radial magnetic field; and
   a control unit, which is at least configured to adjust an excitation voltage of various signal waveforms applied on the primary coil
   and the control unit comprises a function signal generator, an output terminal of the function signal generator being connected to an input terminal of a power amplifier, an output terminal of the power amplifier being connected to the primary coil, wherein the function signal generator is capable of generating an AC signal having a frequency range of 50 to 200 Hz and a voltage level of 10 to 20 Vp-p, the AC signal comprising a sine wave, a triangular wave, a sawtooth wave, a unidirectional square wave, a bidirectional square wave, or a customized function signal, and the power amplifier has a power of 80 to 200 VA, an output AC voltage level of 200 to 400 Vp-p, and a full-power frequency width of 50 to 200 Hz.

2. The inductive magnetoelectric biochemical reaction system according to claim 1, wherein the rotatable magnetic field unit comprises two arc permanent magnets which are fixedly arranged in an annular shape with heteropolars oppositely disposed, a radian of either of the two arc permanent magnets being less than 180 degrees; and a driving mechanism configured to drive the two arc permanent magnets to rotate.

3. The inductive magnetoelectric biochemical reaction system according to claim 2, wherein the arc permanent magnet has a central magnetic flux density of 2000 to 3000 Gs.

4. The inductive magnetoelectric biochemical reaction system according to claim 1, wherein the rotatable magnetic field unit further comprises a detachable iron yoke cylinder, two arc permanent magnets are fixedly arranged in an annular shape on an inner wall of the iron yoke cylinder, and the iron yoke cylinder is connected to a driving mechanism based on transmission, wherein the driving mechanism is configured to drive the two arc permanent magnets to rotate.

5. The inductive magnetoelectric biochemical reaction system according to claim 4, wherein the driving mechanism comprises a servo motor controlled by a servo motor controller which is connected to the iron yoke cylinder.

6. The inductive magnetoelectric biochemical reaction system according to claim 1, wherein the reaction unit further comprises a temperature control unit, configured to control the temperature in the reactant container to −20 to 100° C.

7. The inductive magnetoelectric biochemical reaction system according to claim 6, wherein the temperature control unit comprises a constant temperature circulating water bath which is communicated with a water inlet and a water outlet of a jacket layer on the reaction chamber.

8. The inductive magnetoelectric biochemical reaction system according to claim 1, wherein the primary coil is a single-strand copper wire having a diameter of 6 to 8 mm and having 20 to 26 turns.

9. The inductive magnetoelectric biochemical reaction system according to claim 1, wherein the secondary coil comprises a glass spiral tube having an inner diameter of 2 to 3 mm, having 10 to 13 turns, and having a total length of 700 to 900 mm.

10. The inductive magnetoelectric biochemical reaction system according to claim 1, wherein the closed-loop iron core is made of a silicon steel material and works in a frequency range of 50 to 200 Hz.

11. The inductive magnetoelectric biochemical reaction system according to claim 1 wherein the secondary coil employs a glass spiral tube as a support tube of the conductor of the reaction solution which is connected to two ends of the reactant container to form a communication state, a primary feeding port is arranged on an upper end of the reactant container, a secondary feeding port which is in perpendicular communication with the glass spiral tube is arranged on one side of the reactant container, and a glass jacket which allows circulating liquids with different temperatures to flow through is further arranged on the reaction chamber.

12. A biochemical reaction method, comprising:
   providing the inductive magnetoelectric biochemical reaction system as defined in claim 1 and
   pouring a reaction solution into the reaction unit, applying an AC excitation signal having a frequency of 50 to 200 Hz, a voltage level of 200 to 400 Vp-p and a power of 80 to 200 VA to the primary coil by using the control unit, and causing the rotatable radial magnetic field to rotate at a frequency of 0.1 to 50 Hz, wherein the rotatable radial magnetic field has a central magnetic flux density of 2000 to 3000 Gs.

13. The biochemical reaction method according to claim 12, further comprising:
   generating a sine wave, a triangular wave, a sawtooth wave, a unidirectional square wave, a bidirectional square wave or a customized function signal having a frequency of 50 to 200 Hz and a voltage level of 10 to 20 Vp-p by using a function signal generator, amplifying the signal by using a power amplifier having a power of 80 to 200 VA and a full-power frequency width of 50 to 200 Hz, causing an output AC signal to have a voltage level of 200 to 400 Vp-p, and exciting the primary coil using the output AC signal.

* * * * *